(12) United States Patent
Cushman et al.

(10) Patent No.: US 8,361,133 B2
(45) Date of Patent: Jan. 29, 2013

(54) PATIENT WARMING APPLIQUÉ

(75) Inventors: Barry Michael Cushman, Hudson, MA (US); Robert Kovar, Wrentham, MA (US); Robert Mulligan, Arlington, MA (US); Daniel Babin, Shrewsbury, MA (US); Anna Galea, Stow, MA (US); Jeremiah Slade, Shirley, MA (US); Gordon B. Hirschman, Cohoes, NY (US)

(73) Assignee: Vivonics, Inc., Waltham, MA (US)

( * ) Notice: Subject to any disclaimer, the term of this patent is extended or adjusted under 35 U.S.C. 154(b) by 336 days.

(21) Appl. No.: 12/798,116

(22) Filed: Mar. 30, 2010

(65) Prior Publication Data
US 2010/0280581 A1    Nov. 4, 2010

Related U.S. Application Data

(60) Provisional application No. 61/212,626, filed on Apr. 14, 2009.

(51) Int. Cl.
*A61F 7/00* (2006.01)
(52) U.S. Cl. ............ 607/108; 607/96; 607/112
(58) Field of Classification Search .......... 607/96, 607/104, 108–112, 114
See application file for complete search history.

(56) References Cited

U.S. PATENT DOCUMENTS

| | | | | |
|---|---|---|---|---|
| 3,913,559 | A * | 10/1975 | Dandliker | 126/263.07 |
| 5,662,624 | A * | 9/1997 | Sundstrom et al. | 604/291 |
| 5,984,953 | A | 11/1999 | Sabin et al. | |
| 6,020,040 | A | 2/2000 | Cramer et al. | |
| 6,096,067 | A * | 8/2000 | Cramer et al. | 607/96 |
| 6,116,231 | A | 9/2000 | Sabin et al. | |
| 6,123,717 | A * | 9/2000 | Davis et al. | 607/109 |
| 6,336,935 | B1 * | 1/2002 | Davis et al. | 607/112 |
| 6,576,004 | B2 | 6/2003 | Johnston | |
| 7,041,123 | B2 | 5/2006 | Stapf et al. | |
| 7,878,187 | B2 * | 2/2011 | York-Leung Wong | 126/263.01 |
| 2004/0042965 | A1 * | 3/2004 | Usui et al. | 424/40 |
| 2006/0282138 | A1 * | 12/2006 | Ota | 607/96 |
| 2008/0021530 | A1 | 1/2008 | Castellani et al. | |
| 2008/0093356 | A1 | 4/2008 | Pizzi | |
| 2008/0283038 | A1 * | 11/2008 | Dodo | 126/263.06 |

* cited by examiner

*Primary Examiner* — Roy Gibson
(74) *Attorney, Agent, or Firm* — Iandiorio Teska & Coleman, LLP

(57) ABSTRACT

A patient warming appliqué typically includes a cover layer, a tape layer for releasably securing the appliqué to the patient's skin and an array of encapsulated cells. The encapsulated cells include a chemical heating mechanism beneath the cover layer and a phase change gel sheet between the chemical heating mechanism and the tape layer. The phase change gel sheet is configured to melt and flow when the chemical heating mechanism is activated. The preferred appliqué further includes zones of weakness between the spaced cells allowing the individual cells or a subset of cells to be removed from the appliqué.

38 Claims, 6 Drawing Sheets

PATIENT WARMING APPLIQUÉ

RELATED APPLICATIONS

This application hereby claims the benefit of and priority to U.S. Provisional Application Ser. No. 61/212,626, filed on Apr. 14, 2009 under 35 U.S.C. §§119, 120, 363, 365, and 37 C.F.R. §1.55 and §1.78.

GOVERNMENT RIGHTS

This invention was made with U.S. Government support under Contract No. N00014-05-C-0388 by the U.S. Navy. The Government may have certain rights in certain aspects of the subject invention.

FIELD OF THE INVENTION

The subject invention relates to a patient warming device.

BACKGROUND OF THE INVENTION

Portable hypothermia treatment pads and kits and similar products are known. See U.S. patent application Ser. No. 11/973,704; U.S. Pat. Nos. 6,020,040; 5,984,953; 7,041,123; 6,116,231; 6,576,004 and U.S. patent application Ser. No. 11/491,338. All of these references are hereby incorporated herein by this reference. Known technologies, however, can suffer from several short comings. U.S. Pat. No. 7,041,123, for example discloses only a single warming pack. The separable pockets described in U.S. Pat. No. 6,576,004, in turn, must be soaked in hot water or put in a microwave oven to heat them.

BRIEF SUMMARY OF THE INVENTION

The subject invention features, in one preferred example, a patient warming appliqué including an adhesive tape layer releasably securing the appliqué to the skin of a patient. There is a chemical heating mechanism and a phase change gel sheet to regulate the heat produced by the chemical heating mechanism. There may also be means for separating portions of the appliqué from other portions of the appliqué depending upon the portion of the patient's body to be treated.

This invention features, in one embodiment, a patient warming appliqué which includes a cover layer, a tape layer for releasably securing the appliqué to the patient's skin, and an array of spaced encapsulated cells. The encapsulated cells preferably include a chemical heating mechanism beneath the cover layer and a phase change gel sheet between the chemical heating mechanism and the tape layer. The phase change gel sheet is typically formulated to melt and flow when the chemical heating mechanism is activated.

The appliqué may further include zones of weakness between the spaced cells allowing individual cells or a subset of the cells to be removed. The zones of weakness typically include perforation lines between the spaced cells and the interstices of intersecting perforation lines each include an orifice through the cover layer and the tape layer. The cover layer is preferably gas permeable for activation of the chemical heating mechanism and may include polyurethane. The appliqué may further include a backing layer between the tape layer and the phase change gel sheet. The backing layer also typically includes polyurethane. The appliqué may also include a release layer over the tape layer. A scrim layer may be provided in each cell for supporting the phase change gel sheet. The typical scrim layer includes non-woven polyethylene. Also included in the appliqué may be a separation layer between the chemical heating mechanism and the phase change gel sheet. The separation layer may include polyurethane. The chemical heating mechanism typically includes a compound which is comprised of iron, salt, water, carbon and cellulose, and may be in the form of a powder. The phase change material typically includes an ionic liquid.

The appliqué may include a heat generation rate control layer over all or select openings in the cover layer. One heat generation rate control layer may include a removable film adhered to the cover layer over select openings therein. Another heat generating rate control layer may include a removable semi-permeable film adhered to the cover layer over all or select openings therein. In one example, the heat generating rate control layer may include a removable film with orifices therethrough smaller than the openings in the cover layer. The removable film is typically adhered to the cover layer over all or select openings therein.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
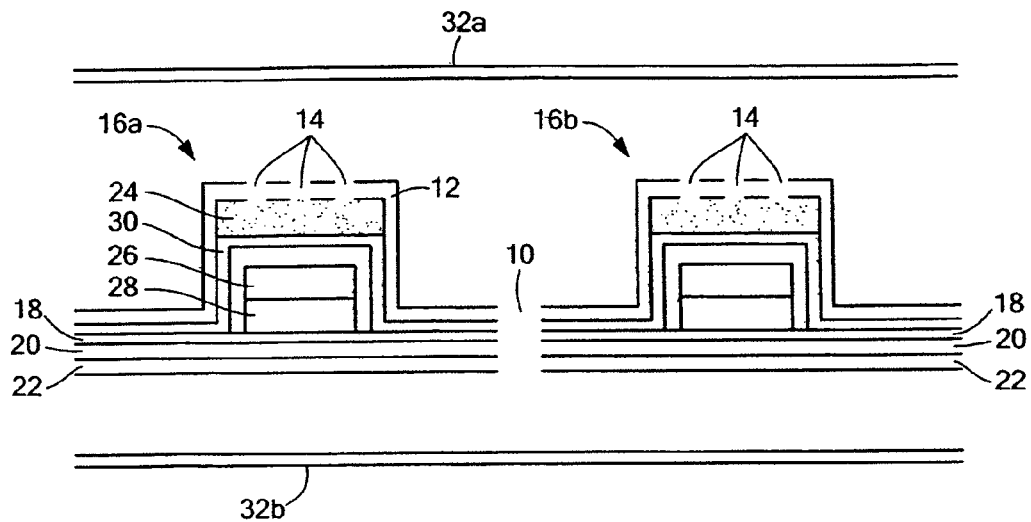
FIG. 1 is a highly schematic cross-sectional side view showing an embodiment of a patient warming device (PWD) or appliqué system in accordance with an example of the subject invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

The subject invention features a warming device that can be implemented by medics on critically wounded patients (battlefield injuries, car accidents, etc.) to prevent the onset of hypothermia and increased mortality rates associated with departures from normothermia. There is existing technology for this purpose, most notable the Hypothermia Prevention Management Kit (HPMK) produced by NARP, and the Ready-Heat blanket. The subject invention is an improved product because is has customized fit, removable modules for wound access, and incorporates phase change materials to better regulate the output of generated heat. The preferred device is a non-invasive disposable product that can be characterized as 'class 1' hot/cold pack for FDA regulatory purposes.

The subject invention, in one example, features conformity to the victim's body as it is ergonomically shaped. The appliqué is adhered to the victim's skin for optimal heat transfer, and contains a phase change material layer to stabilize the temperature output to 104° F. The phase change material typically includes an ionic liquid, or a commercially available petroleum product such as Astorphase 40B or 42B. The subject invention also contains perforated or permeable packing material that surrounds an iron-based air activated heating chemistry. The subject invention also has perforation such that modules can be removed for wound access or customized sizing. The device may be designed such that the left torso section is the same as the right thigh, and the right torso section is the same as the left thigh.

One application of the invention is combat casualty care where prevention of hypothermia in trauma victims during transport to medical care is important for survivability.

In one best mode, there are two torso units (left/right) and two thigh units (left/right). The units are ergonomically shaped for comfort and efficient heat delivery, and are adhered directly to the skin. Perforations are present between the heat cells to enable a medic to tear portions off such that wound access is maintained. The product is designed such that the left torso section is also the right thigh section, and the right torso section is also the left thigh section. This enables less expensive manufacturing and flexibility for the medic in applying the sections. Casualty care and body temperature regulation for traumatically injured patients in civilian and military settings is possible. A military field medic or corpsman will carry this in his/her equipment pouch for rapid deployment in the battlefield. When encountering a casualty, the medic removes the PWD from its packaging, unfolds it, and adheres to the torso and thighs of the patient. A civilian EMT will carry several PWDs in an ambulance at all times. When arriving at the scene of a car accident or other event with injuries, the EMT will immediately implement the PWD to the victim to prevent a dangerous drop in body temperature. In both cases, the shape of the PWD can be modified by tearing at perforations to leave access to wound sites. The PWD can be customized to provide heat generation for up to 8 hours depending on the use scenario. The subject invention preferably conforms to the body shape for comfort and maximum heat delivery; it is modular so that the medic can tear off perforated sections to enable wound access; has separate torso and thigh modules, and utilizes an ionic liquid as a phase change material which regulates/tempers the heat output to the body.

Existing products for hypothermia management are poorly engineered. Essentially, they are comprised of materials assembled in the form of a large rectangle that encase loose exothermic heating material. These feel like bags of sand. They are cumbersome and inefficient. Some products integrate a reflective, metallized 'space blanket' to the object to enhance heat reflection to the patient. Anecdotally speaking, these are reported to get too hot. The specific challenges and requirements presented by the military resulted in a creative design approach and material selection process. The phase change material is cast into desired shapes and thickness with supporting material such as non-woven polyethylene 'scrim.' Multiple blocks of the phase change material are arranged and sealed between two layers of polymer or aluminum packing, and the part is die cut to the desired final shape. One side of the packaging has a skin-safe (FDA approved) double sided tape with a release liner for future attachment to a person. The chemical heating element (powder or cake) is placed above the arranged phase change material sections (non-adhesive side), and a third layer of packaging is sealed in place. The third layer has a predescribed oxygen permeability made possible by laser drilling, mechanical perforations, or micro porous membranes. The final assembly is perforated in between the heater sections along the seals, and placed in an airtight package for storage. Test samples of 9-segment prototype warming devices have been tested with customized thermo-sensing pads. The product can be utilized by field medics in wartime situations to treat casualties. Alternatively, the product can be carried in an ambulance and deployed when necessary.

In one example, the polymer film layers are 3.0 mil polyurethane. The adhesive is Avery 600. The ionic liquid is 905LA (Nanotechlabs). Approximately 4.5 grams of ionic liquid are used per segment. The heating mechanism includes 8.68 grams of powder per segment. The powder may be 39.37% iron, 2.37% salt, 31.50% water, 15.75% carbon and 11.02% cellulose fluff. The respective mass ratios are 3.42, 0.21, 2.73, 1.37, and 0.96.

Figure 2:
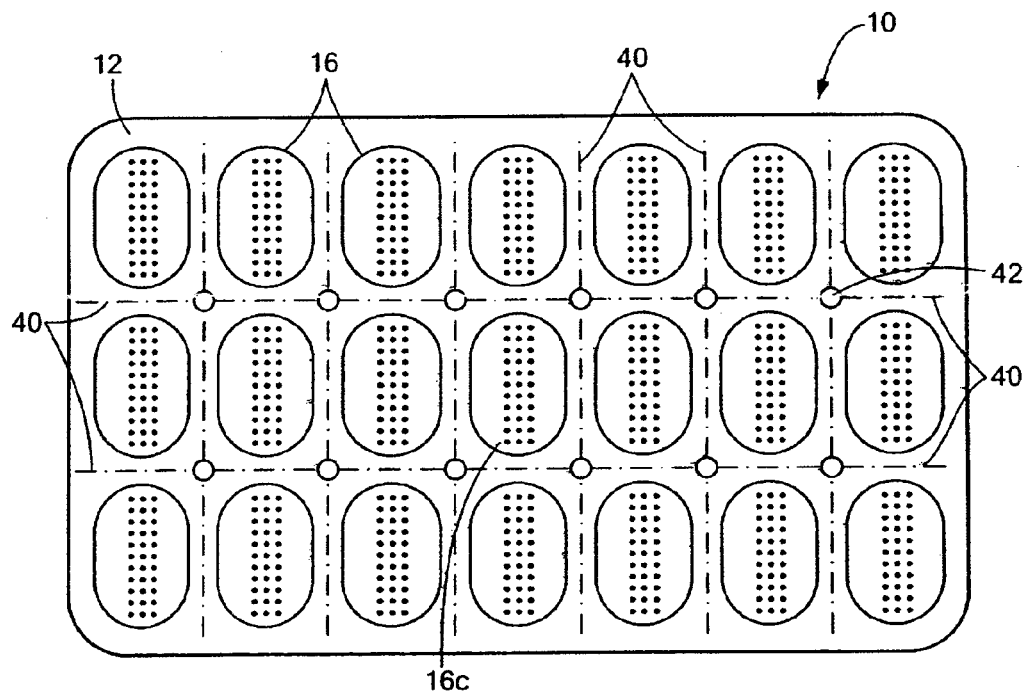
FIG. 2 is a schematic top view of the appliqué shown in FIG. 1.

FIGS. 1-2 depict one preferred example of appliqué 10 in accordance with the subject invention. There is a cover layer 12 with openings 14 therein at least in the region of cells 16a and 16b rendering the cover layer gas permeable. Backing layer 18 has double sided tape layer 20 on it and release layer 22 protects tape layer 20 until the appliqué is ready to be used.

Each cell 16 in the array is encapsulated between cover layer 12 and backing layer 18 as shown and houses chemical heating mechanism 24 beneath cover layer 12 and phase change gel sheet 26 supported by scrim 28. Gel sheet 26 is typically separated from chemical heating mechanism 25 by separation layer 30. Gel sheet 26 is configured (e.g., formulated) to change from a solid wax-like substance to a flowing substance when its temperature is raised due to the activation of chemical heating mechanism 24 when appliqué 10 is removed from gas impermeable package 32 (including, for example, layer 32a sealed to layer 32b). When this happens in the field, air activates chemical heating mechanism 24 and its temperature rises to a predetermined temperature. At or near that temperature, gel sheet 26 flows tempering the heat applied to the patient's skin.

Perforation lines 40 between the spaced cells of the array allow individual cells 16 or a subset of all the cells to be removed from the appliqué for use in the field. At the interstices of intersecting perforation lines 10 are orifices 42 through all the layers. These orifices make it easier to remove interior cells such as cell 16c in FIG. 2 so the appliqué applied to the patient's skin does not interfere with a wound, for example, or the treatment of the wound. The remaining cells of the appliqué would thus be positioned around the wound. The result is a highly versatile, easy to use warming appliqué.

Cover layer 12, FIG. 1, backing layer 18, and separation layer 30 may all be made of polyurethane and are typically approximately 3.0 mils thick. Tape layer 20 may be a double sided tape such as the Avery 6000 double sided tape. Chemical heating mechanism 24 may be a powder comprising iron, salt, water, carbon, and cellulose. When activated, it is desirable for the heating mechanism to reach between 100°-104° F. Phase change layer 26 typically includes an ionic liquid based on lauric acid. The phase change layer generally melts and flows at temperatures around 100°-104° F. when the chemical heating mechanism 10 activates to temper the heat applied to the patient. Scrim layer 28 may be non-woven polyethylene material.

The monolithic sheet of waxy or gelatinous phase change material is more dense and uniform than layers consisting of phase change materials in particulate form. This new configuration confers several advantages to the subject invention including larger thermal storage capacity and improved uniformity and heat transfer. The result is enhanced protection against hotspots and burns. Also, since there are no air gaps, the resulting appliqué can be more compact than a device using phase change material in particulate form. Such enhancements to safety and stowability are advantageous when it comes to selecting medical devices for first responders and battlefield medics.

Figure 3:
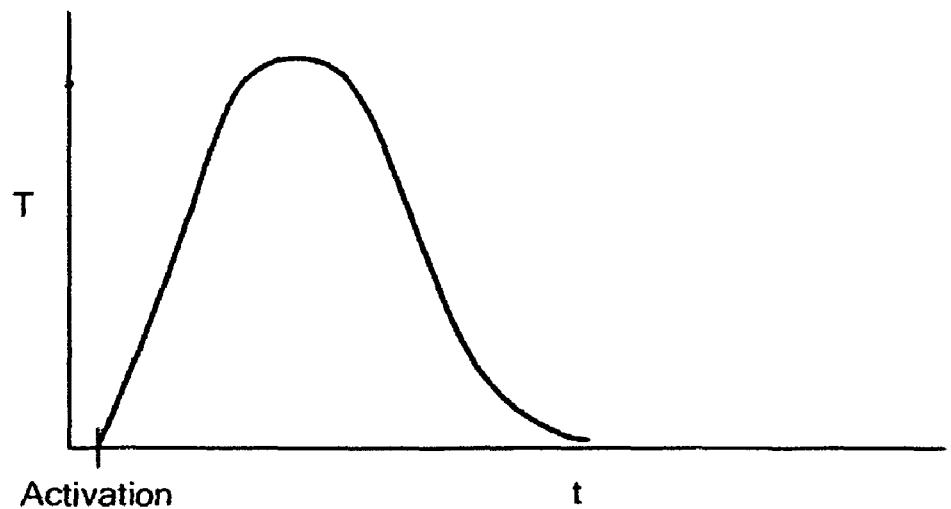
FIG. 3 is a graph showing the temperature of a prior art warming apparatus over time.
Figure 4:
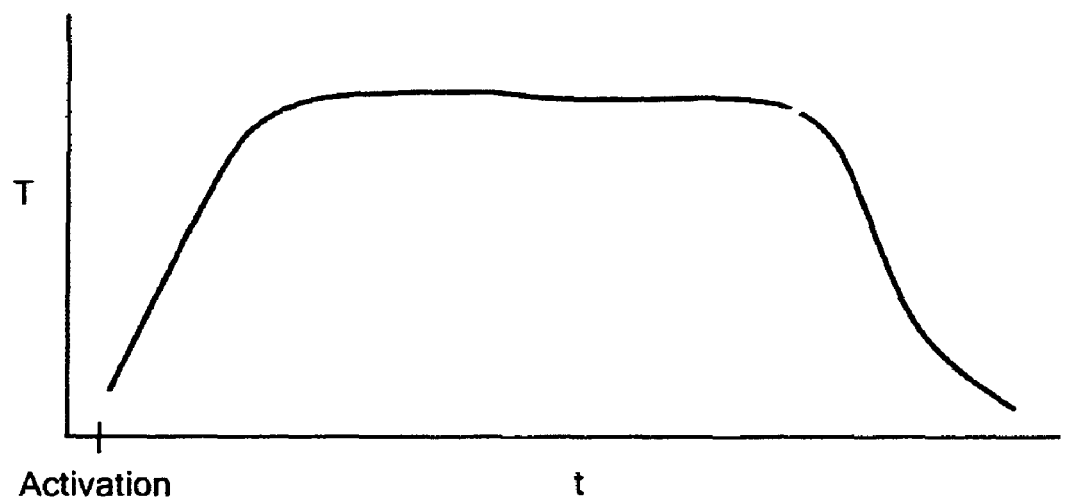
FIG. 4 is a graph showing temperature as a function of time for an embodiment of the patient warming appliqué of the subject invention.

FIG. 3 depicts how prior art heating packs without any heat regulating technology quickly warm up at activation and then quickly cool. FIG. 4 depicts how the phase change gel sheet 26, FIG. 1 better regulates the heat generated by chemical heating mechanism 24.

Figure 5:
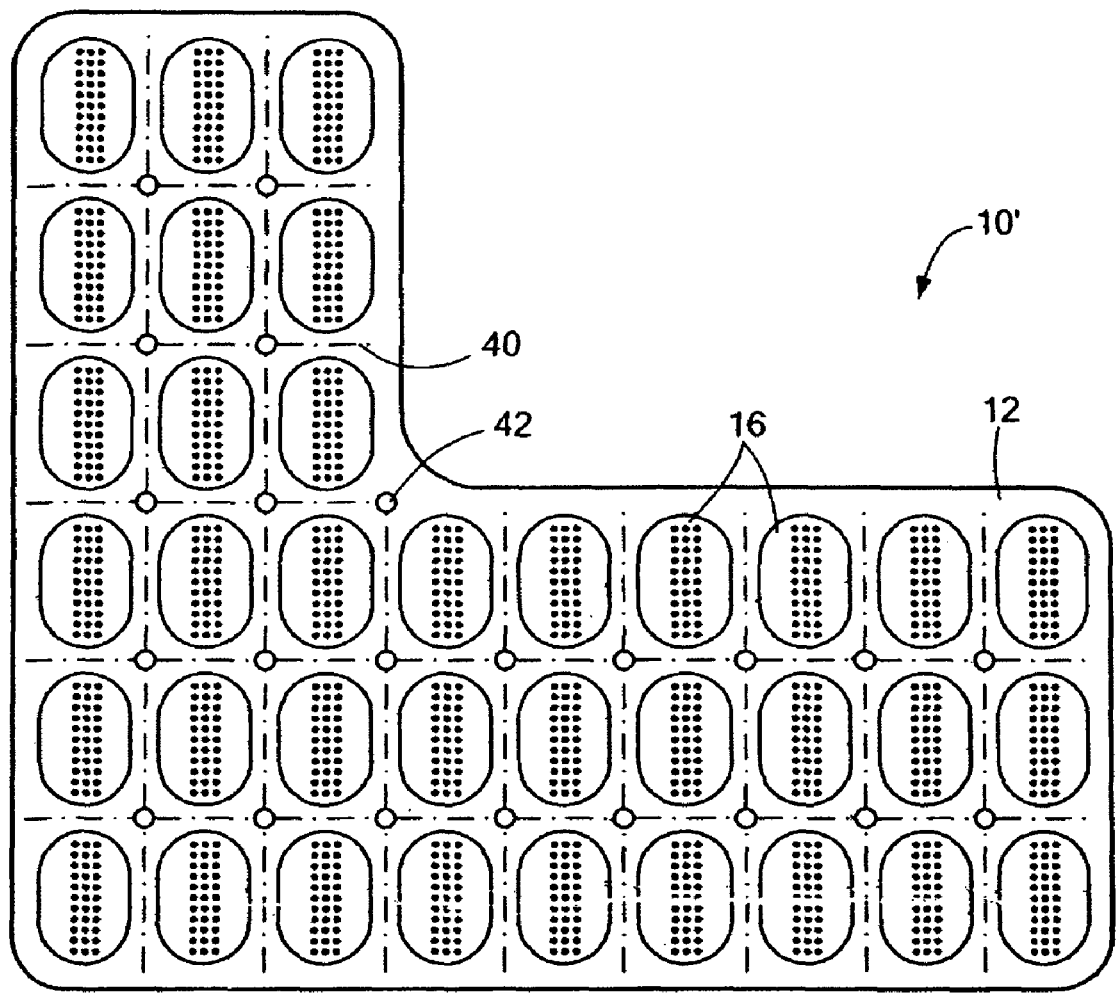
FIG. 5 is a schematic top view showing another example of an appliqué in accordance with the subject invention.
Figure 6:
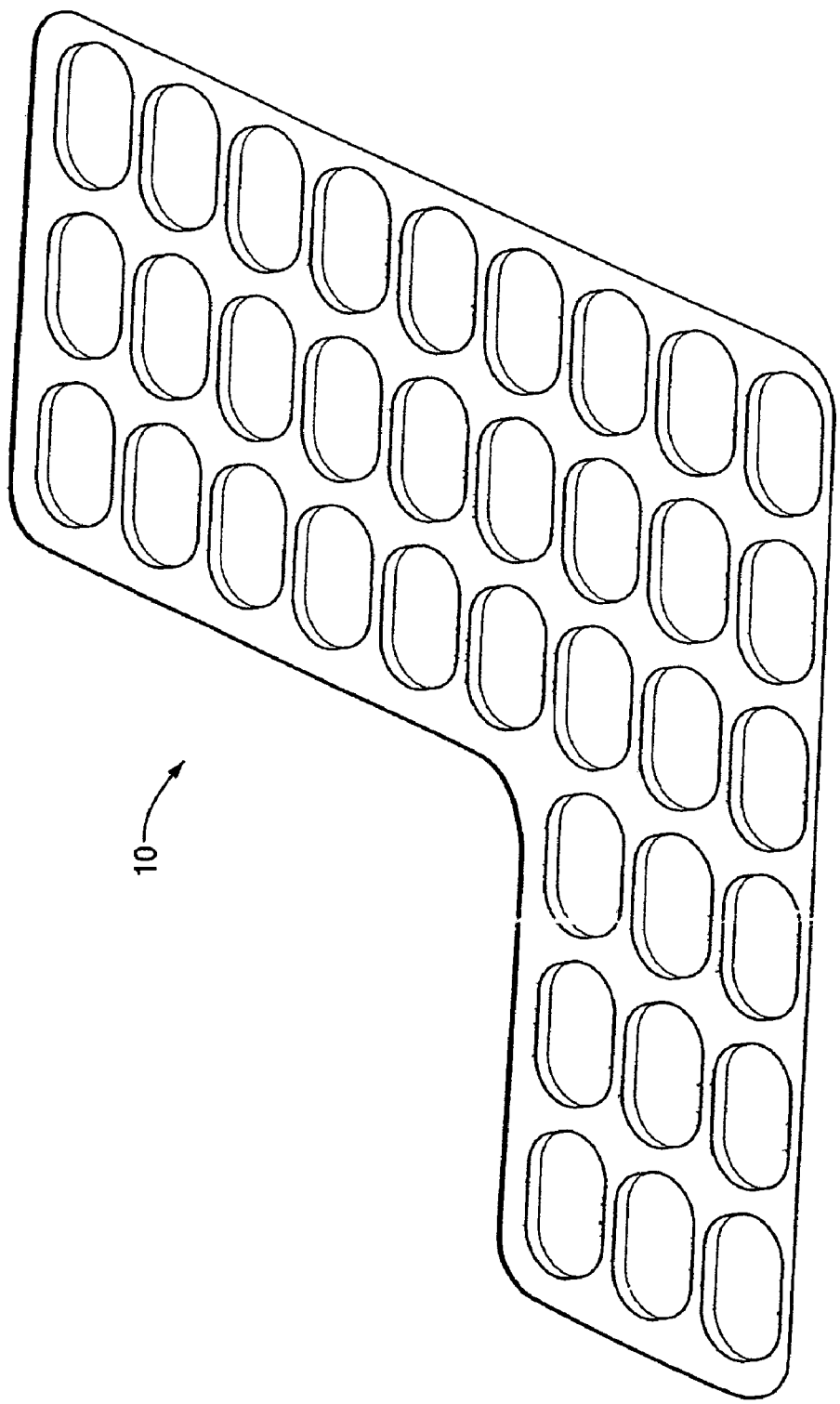
FIG. 6 is another schematic top view of the appliqué shown in FIG. 5.
Figure 7:
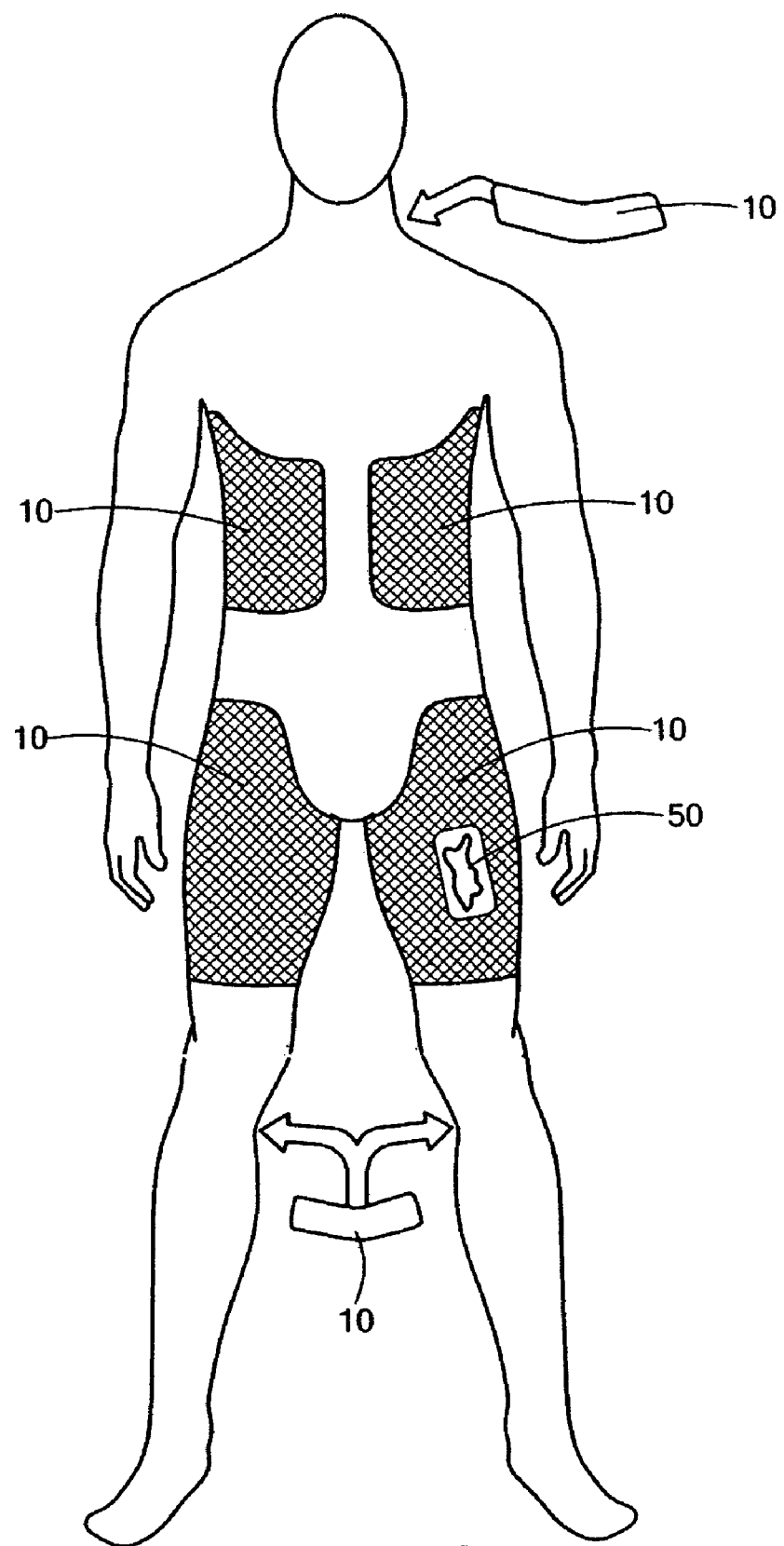
FIG. 7 is a schematic view showing appliqué's in accordance with the subject invention applied to a patient's skin in various locations.

In FIGS. 5-6, appliqué 10 has a "L" shape and is approximately 18.5 inches tall, 20.03 inches long and includes cells 16.25 inches thick and 2.50 inches long and 1.67 inches wide. FIG. 7 depicts how such appliqués and/or a subset of the cells can be applied to sections of the human body even about wound 50 as discussed above.

Figure 8:
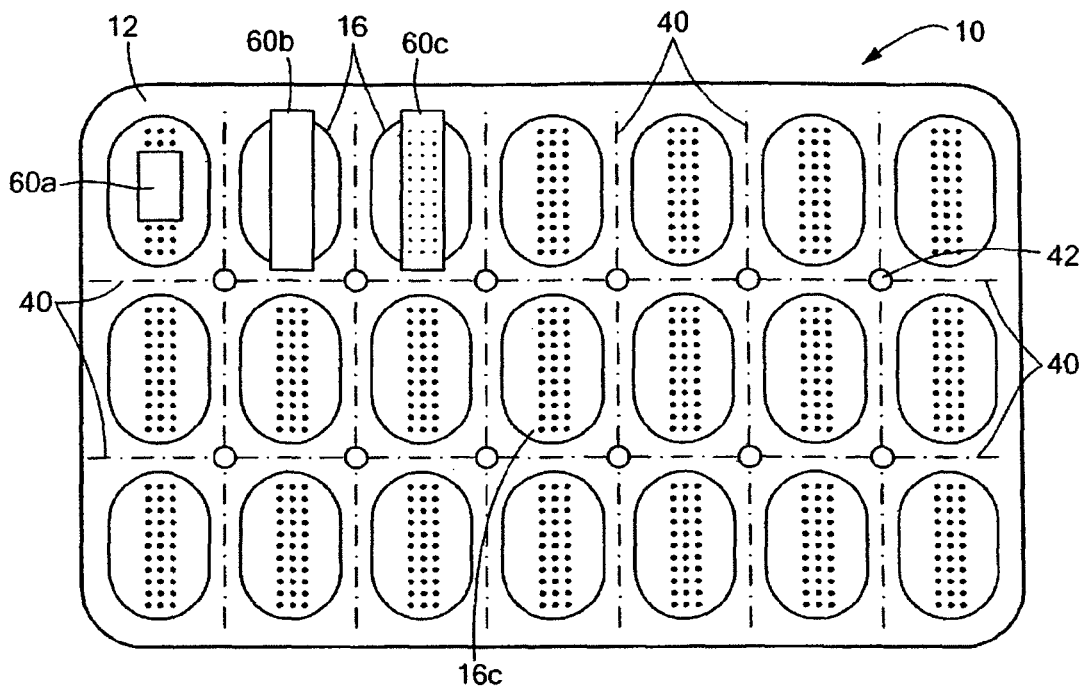
FIG. 8 is a schematic top view of another example of an appliqué in accordance with this invention.
Figure 9A:
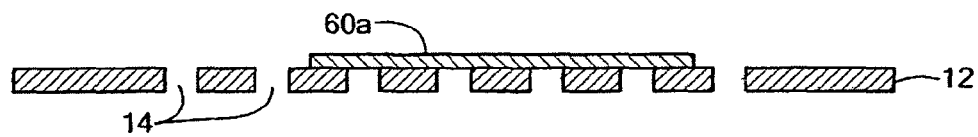
FIG. 9A-9C are side cross-sectional views showing three versions of a heat generation rate control layer which can be used in embodiments of this invention.
Figure 9B:
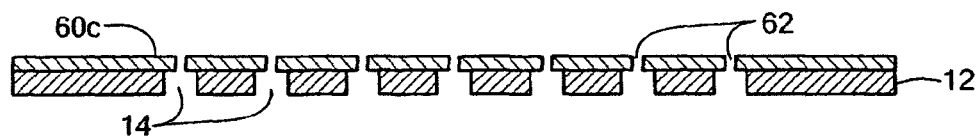
Figure 9C:
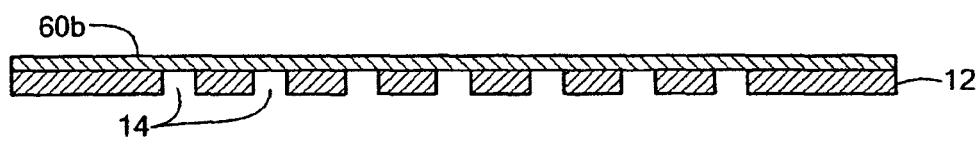

In one embodiment, each cell, FIG. 8, includes on cover layer, FIGS. 9A-9C, a heat generation rate control layer 60a, 60b, and/or 60c. Control layer 60a, FIG. 9A, covers select openings 14 in cover layer 12 and may be removed partially or completely to increase the heat generation rate. Control layer 60b, FIG. 9C, is semi-permeable and can be removed partially or completely to increase the heat generation rate. Control layer 60c, FIG. 9B, has openings 62 smaller than the openings 14 in cover layer 12. Again, control layer 60c can be partially or completely removed to increase the heat generation rate. Layers 60a-60c may be thin adhesive backed films made of plastic. Layer 60b can be made of a breathable polyurethane film.

In this way, the heat generation rate of heating mechanism 24, FIG. 1 can be controlled by regulating the amount of air which reaches heating mechanism 24 after cover layers 32a, 32b are removed in the field.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

What is claimed is:

1. A patient warming appliqué system comprising:
   an appliqué including:
   a cover layer with openings therein,
   a backing layer,
   a tape layer on the backing layer for releasably securing the appliqué to the patient's skin,
   a release layer over the tape layer,
   an array of spaced encapsulated cells each including:
   a chemical heating mechanism beneath the cover layer,
   a separation layer under the chemical heating mechanism, and
   a phase change gel sheet between the separation layer and the backing layer, the phase change gel sheet formulated to melt when the chemical heating mechanism is activated, and
   a scrim layer supporting the gel sheet;
   zones of weakness between the spaced cells allowing individual cells or a subset of the cells to be removed from the appliqué, the zones of weakness including perforation lines between the spaced cells, the interstices of intersecting perforating lines each including an orifice through the layers; and
   a gas impermeable package about the appliqué.

2. The appliqué of claim 1 further including a heat generation rate control layer over all or select openings in the cover layer.

3. The appliqué of claim 2 in which the heat generation rate control layer includes a removable film adhered to the cover layer over select openings therein.

4. The appliqué of claim 2 in which the heat generating rate control layer includes a removable semi-permeable film adhered to the cover layer over all or select openings therein.

5. The appliqué of claim 2 in which the heat generating rate control layer includes a removable film with orifices therethrough smaller than the openings in the cover layer, the removable film adhered to the cover layer over all or select openings therein.

6. The appliqué of claim 5 further including a backing layer between the tape layer and phase change gel sheet.

7. A patient warming appliqué comprising:
   a cover layer;
   a tape layer for releasably securing the appliqué to the patient's skin;
   an array of spaced encapsulated cells each including:
   a chemical heating mechanism beneath the cover layer formulated to reach at least a temperature T when activated, and
   a phase change gel sheet between the chemical heating mechanism and the tape layer, the phase change gel sheet formulated to melt at temperature T; and
   zones of weakness between the spaced cells allowing individual cells or a subset of the cells to be removed from the appliqué.

8. The appliqué of claim 7 in which the zones of weakness include perforation lines between the spaced cells, the interstices of intersecting perforation lines each including an orifice through the cover layer and the tape layer.

9. The appliqué of claim 7 in which cover layer is gas permeable for activation of the chemical heating mechanism.

10. The appliqué of claim 7 in which the cover layer includes polyurethane.

11. The appliqué of claim 7 further including a release layer over the tape layer.

12. The appliqué of claim 11 in which the compound is in the form of a powder.

13. The appliqué of claim 7 further including a scrim layer in each cell supporting the phase change gel sheet.

14. The appliqué of claim 13 in which the scrim layer includes a non-woven polyethylene material.

15. The appliqué of claim 7 further including a separation layer between the chemical heating mechanism and the phase change gel sheet.

16. The appliqué of claim 15 in which the separation layer includes polyurethane.

17. The appliqué of claim 7 in which the chemical heating mechanism includes a compound comprising iron, salt, water, carbon and cellulose.

18. The appliqué of claim 7 in which the phase change material includes an ionic liquid.

19. The appliqué of claim 7 in which the cover layer includes openings therein.

20. The appliqué of claim 19 further including a heat generation rate control layer over all or select openings in the cover layer.

21. The appliqué of claim 20 in which the heat generation rate control layer includes a removable film adhered to the cover layer over select openings therein.

22. The appliqué of claim 20 in which the heat generating rate control layer includes a removable semi-permeable film adhered to the cover layer over all or select openings therein.

23. The appliqué of claim 20 in which the heat generating rate control layer includes a removable film with orifices therethrough smaller than the openings in the cover layer, the removable film adhered to the cover layer over all or select openings therein.

24. A patient warming appliqué comprising:
   a cover layer;
   a tape layer for releasably securing the appliqué to the patient's skin; and
   an array of spaced encapsulated cells, each including:
      a chemical heating mechanism beneath the cover layer, and
      a phase change gel sheet between the chemical heating mechanism and the tape layer, the phase change gel sheet configured to melt and flow when the chemical heating mechanism is activated; and
      zones of weakness between the spaced cells allowing individual cells or a subset of the cells to be removed from the appliqué.

25. The appliqué of claim 24 in which the zones of weakness include perforation lines between the spaced cells, the interstices of intersecting perforation lines each including an orifice through the cover layer and the tape layer.

26. The appliqué of claim 24 further including a backing layer between the tape layer and phase change gel sheet.

27. The appliqué of claim 24 further including a release layer over the tape layer.

28. The appliqué of claim 24 further including a scrim layer in each cell supporting the phase change gel sheet.

29. The appliqué of claim 24 further including a separation layer between the chemical heating mechanism and the phase change gel sheet.

30. The appliqué of claim 24 in which the chemical heating mechanism includes a compound comprising iron, salt, water, carbon and cellulose.

31. The appliqué of claim 24 in which the phase change material includes an ionic liquid.

32. The appliqué of claim 24 in which the cover layer includes openings therein.

33. The appliqué of claim 32 further including a heat generation rate control layer over all or select openings in the cover layer.

34. The appliqué of claim 32 in which the heat generation rate control layer includes a removable film adhered to the cover layer over select openings therein.

35. The appliqué of claim 32 in which the heat generating rate control layer includes a removable semi-permeable film adhered to the cover layer over all or select openings therein.

36. The appliqué of claim 32 in which the heat generating rate control layer includes a removable film with orifices therethrough smaller than the openings in the cover layer, the removable film adhered to the cover layer over all or select openings therein.

37. A patient warming appliqué comprising:
   a cover layer;
   a tape layer for releasably securing the appliqué to the patient's skin; and
   an array of spaced encapsulated cells each including:
      a chemical heating mechanism beneath the cover layer formulated to reach at least a temperature T when activated, and
      a phase change gel sheet including an ionic liquid, the phase change gel sheet between the chemical heating mechanism and the tape layer and formulated to melt at temperature T.

38. A patient warming appliqué comprising:
   a cover layer including openings therein;
   a heat generation rate control layer over all or select openings in the cover layer;
   a tape layer for releasably securing the appliqué to the patient's skin; and
   an array of spaced encapsulated cells each including:
      a chemical heating mechanism beneath the cover layer formulated to reach at least a temperature T when activated, and
      a phase change gel sheet between the chemical heating mechanism and the tape layer, the phase change gel sheet formulated to melt at temperature T.

* * * * *